US00PP12610P2

(12) United States Plant Patent
Koppe

(10) Patent No.: US PP12,610 P2
(45) Date of Patent: May 7, 2002

(54) BEGONIA PLANT NAMED 'BENO'

(75) Inventor: Lubbertus H. Koppe, Ermelo (NL)

(73) Assignee: Koppe Veredeling B.V., Ermelo (NL)

( * ) Notice: Subject to any disclaimer, the term of this patent is extended or adjusted under 35 U.S.C. 154(b) by 0 days.

(21) Appl. No.: 09/641,720

(22) Filed: Aug. 21, 2000

(51) Int. Cl.[7] ..... A01H 5/00
(52) U.S. Cl. ..... Plt./349
(58) Field of Search ..... Plt./349

(56) References Cited
PUBLICATIONS
UPOV–ROM GTITM Computer Database 2001/03, GTI Jouve Retrieval Software, citation for 'Beno'.*
* cited by examiner

*Primary Examiner*—Bruce R. Campell
*Assistant Examiner*—Anne Marie Grünberg
(74) *Attorney, Agent, or Firm*—C. A. Whealy

(57) ABSTRACT

A new and distinct cultivar of Begonia plant named 'Beno', characterized by its compact and freely branching plant habit; fully double red flowers; short peduncles and short pedicels; and excellent postproduction longevity.

2 Drawing Sheets

BACKGROUND OF THE INVENTION

The present Invention relates to a new and distinct cultivar of Begonia plant, botanically known as Begonia×hiemalis, commercially known as Elatior Begonia, and hereinafter referred to by the name 'Beno'.

The new Begonia was discovered by the Inventor in a controlled environment in Ermelo, The Netherlands, in April, 1994, as a naturally-occurring whole plant mutation of *Begonia×hiemalis* 'Bellona', disclosed in U.S. Plant Pat. No. 10,476. The new Begonia was observed as a single plant in a group of flowering plants of the parent cultivar. The selection of this plant was based on its unique flower color and plant size.

Asexual reproduction of the new Begonia by leaf and terminal cuttings taken in a controlled environment in Ermelo, The Netherlands, has shown that the unique features of this new Begonia are stable and reproduced true to type in successive generations.

SUMMARY OF THE INVENTION

The cultivar 'Beno' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Beno'. These characteristics in combination distinguish 'Beno' as a new and distinct Begonia:

1. Compact and freely branching plant habit.
2. Fully double red-colored flowers.
3. Short peduncles and short pedicels.
4. Excellent postproduction longevity.

In side-by-side comparisons conducted by the Inventor in Ermelo, The Netherlands, plants of the new Begonia differ from plants of the parent cultivar Bellona in the following characteristics:

1. Plants of the new Begonia are more compact than plants of the cultivar Bellona.

2. Flower color of plants of the new Begonia is more intense red than flower color of plants of the cultivar Bellona.
3. Plants of the new Begonia have smaller leaves and flowers than plants of the cultivar Bellona.
4. Plants of the new Begonia have shorter peduncles and shorter pedicels than plants of the cultivar Bellona.

BRIEF DESCRIPTION OF THE PHOTOGRAPHS

The accompanying colored photographs illustrate the overall appearance of the new Begonia, showing the colors as true as it is reasonably possible to obtain in colored reproductions of this type. Colors in the photographs may differ slightly from the color values cited in the detailed botanical description which more accurately describe the actual colors of the new Begonia.

The photograph on the first sheet comprises a side perspective view of a typical flowering plant of 'Beno'.

The photographs on the second sheet, from top to bottom, are close-ups of the upper surfaces of typical developing flowers, the lower surfaces of typical developing flowers, the upper surfaces of typical developing leaves, and the lower surfaces of typical developing leaves of 'Beno'.

DETAILED BOTANICAL DESCRIPTION

In the following description, color references are made to The Royal Horticultural Society Colour Chart except where general terms of ordinary dictionary significance are used. The following observations and measurements describe plants grown in Ermelo, The Netherlands, under commercial practice in a glass-covered greenhouse. Average day and night temperatures were 20° C. during the first three to four weeks then lowered to an average day and night temperature of 19° C. until flowering. Four weeks after planting in 12-cm containers, one week of long nyctoperiods were given followed by short nyctoperiods of eight hours. Measurements and numerical values represent averages for typical flowering plants.

Botanical classification: *Begonia×hiemalis* cultivar Beno.
Commercial classification: Elatior Begonia.

Parentage: Naturally-occurring whole plant mutation of *Begonia×hiemalis* cultivar Bellona, disclosed in U.S. Plant Pat. No. 10,476.

Propagation:

*Type.*—Terminal cuttings.

*Time to develop roots.*—About 42 days with soil temperatures of 20° C.

*Root description.*—Fine, fibrous and well-branched; plants typically do not form tubers.

Plant description:

*Plant form.*—Compact; upright and rounded potted plant; freely branching with good stem and stem base strength. Flowers are fully double and abundant. Plants flower continuously.

*Growth habit.*—Moderate growth rate, vigorous. Suitable for 9 to 15-cm containers. Under optimal environmental and cultural conditions, usually about 4 months are required to produce proportional 13-cm potted plants from terminal cuttings. Vegetative shoots are formed at basal nodes and flowering shoots are formed at upper nodes.

*Plant height.*—About 22.5 cm.

*Plant width.*—About 26 cm.

*Leaves.*—Arrangement: Simple, alternate. Length: About 9 cm. Width: About 8.5 cm. Shape: Asymmetrical, more or less reuniform. Apex: Acuminate. Base: Cordate. Margin: Doubly serrate. Texture: Glabrous. Petiole length: About 4 cm. Color, young and fully expanded leaves: Upper surface: 147A. Lower surface: 194A. Venation: 144B. Petiole: 166C.

Flower description:

*Flowering habit.*—Fully double flowers with numerous tepals arranged in axillary cymes. Usually 8 to 12 flowers per cyme. Many cymes in flower simultaneously. Flowering continuous.

*Natural flowering season.*—Plants will flower year around regardless of nyctoperiod, however plants flower earlier and more abundantly from mid-February until November in the Northern Hemisphere.

*Flowers.*—Shape: Rounded. Diameter: About 5 cm. Depth (height): About 2 cm.

*Flower buds.*—Length: About 1.5 cm. Diameter: About 1.2 cm. Color: 60A.

*Tepals.*—Arrangement: Rosette. Shape: Rounded flabellate; apex, rounded. Margin: Slightly crenate. Quantity per flower: Usually about 30 per flower. Size: Outer tepals: Length: About 2.4 cm. Width: About 2.4 cm. Inner tepals: Length: About 1.7 cm. Width: About 1.5 cm. Texture: Smooth, satiny, glabrous. Color: When opening: 43A. Fully opened, upper surface: 43A. Fully opened, lower surface: 43B to 43 C.

*Flower bracts.*—Arrangement: Two opposite. Shape: Broadly cordate; apex, apiculate. Margin: Serrate. Color, both surfaces: 139D with anthocyanin.

*Peduncles.*—Angle: Erect. Length: About 4.5 cm. Texture: Glabrous. Color: 146D.

*Pedicels.*—Angle: Erect. Length: About 1.2 cm. Texture: Pubescent. Color: 180A.

*Reproductive organs.*—Stamens: None observed. Pistils: None observed.

*Seed.*—Seed production has not been observed as reproductive organs are not formed.

Postproduction longevity:

*Individual flowers.*—Generally about 2 to 3 weeks.

*Whole plants.*—About 6 weeks under interior conditions.

Disease resistance: Resistance to diseases common to Begonia has not been determined.

It is claimed:

1. A new and distinct cultivar of Begonia plant named 'Beno', as illustrated and described.

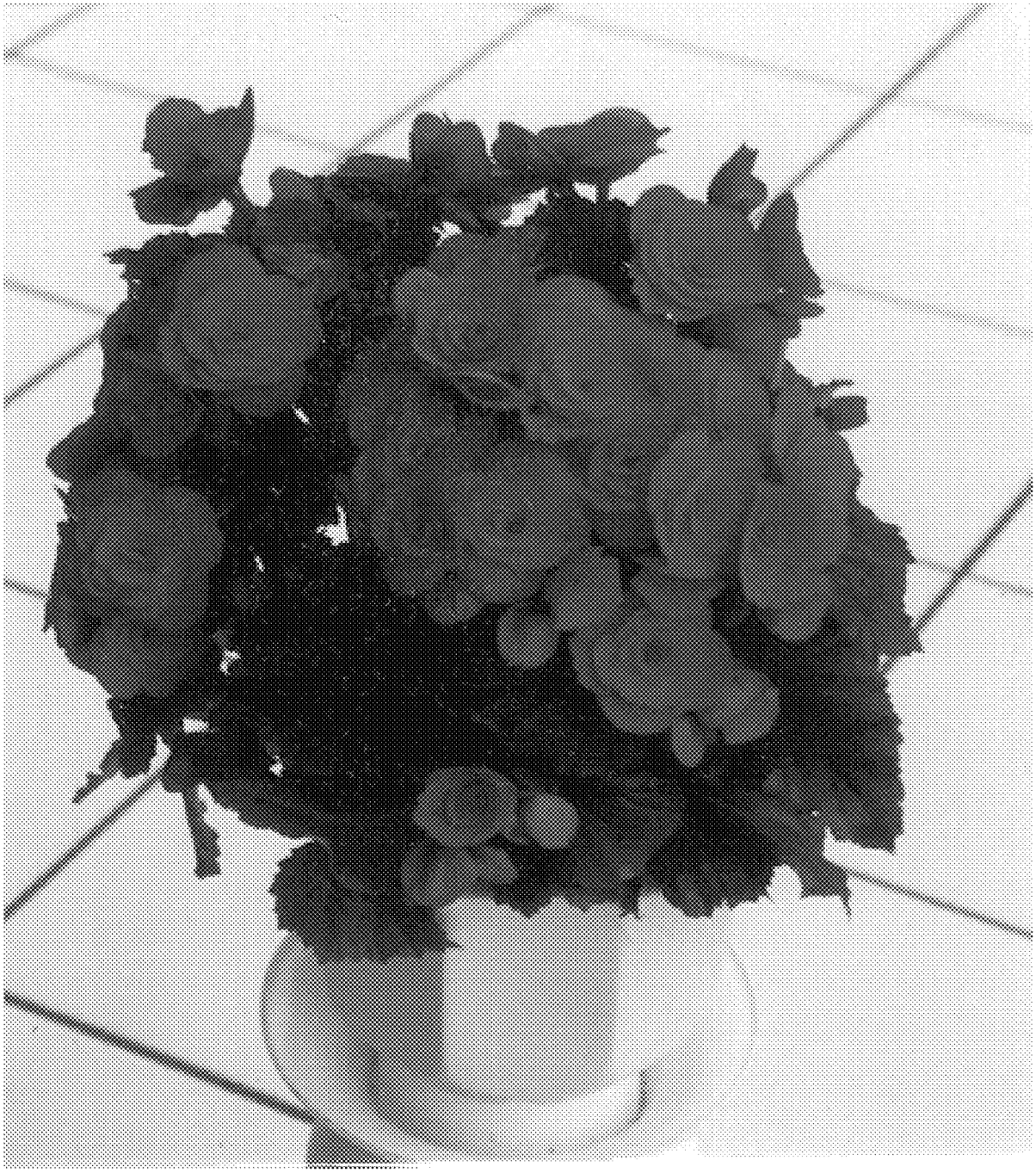

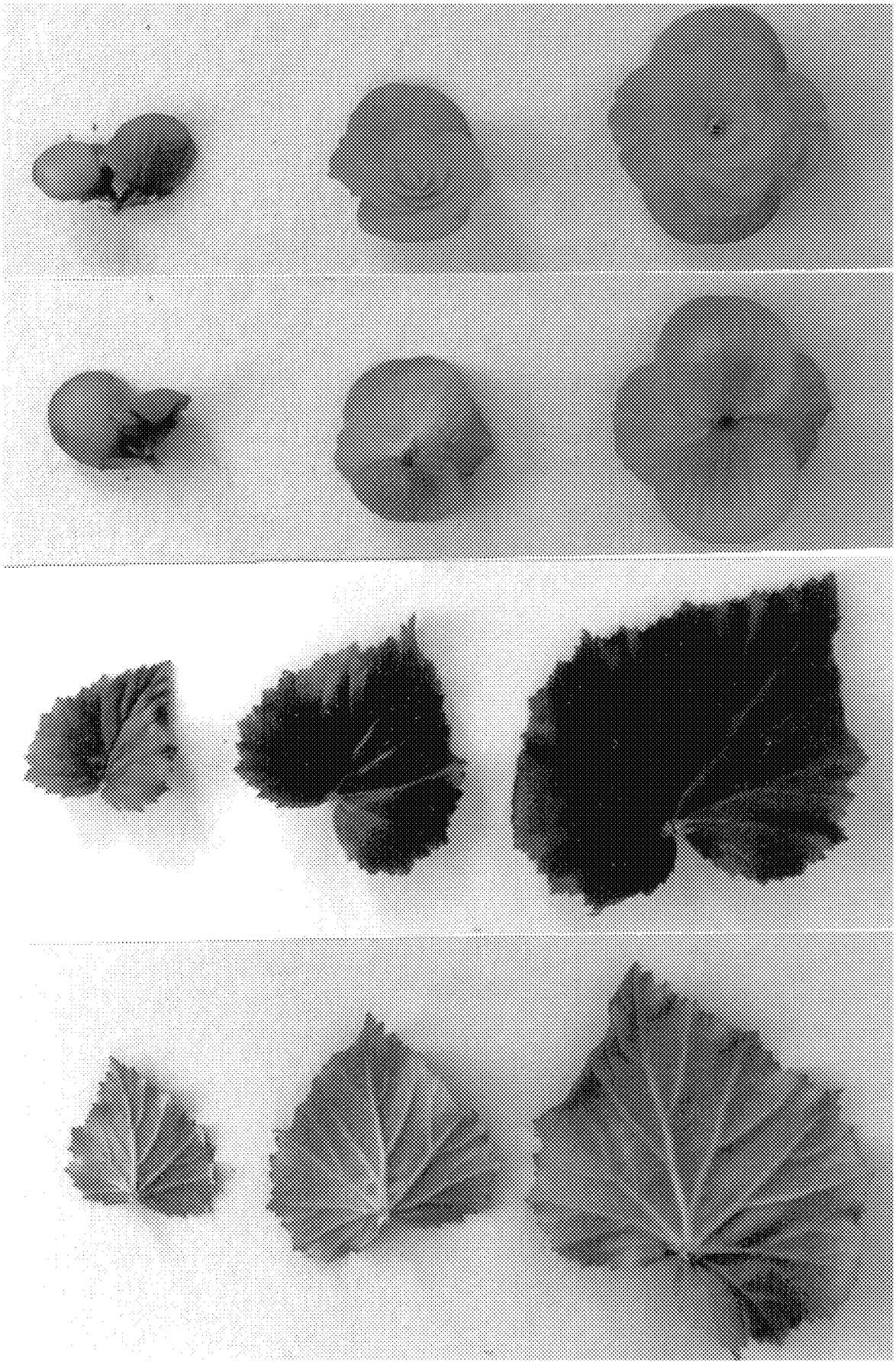

* * * * *